United States Patent [19]

Neuwelt

[11] Patent Number: 4,866,042
[45] Date of Patent: Sep. 12, 1989

[54] METHOD FOR THE DELIVERY OF GENETIC MATERIAL ACROSS THE BLOOD BRAIN BARRIER

[76] Inventor: Edward A. Neuwelt, 4246 SW. McDonnell Ter., Portland, Oreg. 97201

[21] Appl. No.: 122,027

[22] Filed: Nov. 18, 1987

[51] Int. Cl.$^4$ .................... A61K 35/76; A61K 39/00; A61K 39/21; A61K 45/05
[52] U.S. Cl. ........................................ 514/44; 435/91; 435/172.2; 935/52; 935/53
[58] Field of Search ..................... 514/44; 935/52, 53; 435/172, 91

[56] References Cited

U.S. PATENT DOCUMENTS

| | | | |
|---|---|---|---|
| 4,351,831 | 9/1982 | Growdon et al. | 424/199 |
| 4,363,793 | 12/1982 | Blau et al. | 424/1 |
| 4,479,932 | 10/1984 | Bodor | 424/9 |
| 4,622,218 | 11/1986 | Bodor | 424/9 |
| 4,624,846 | 11/1986 | Goldenberg | 424/1.1 |
| 4,634,586 | 1/1987 | Goodwin et al. | 424/1.1 |

OTHER PUBLICATIONS

Abe et al., "Changes in Cerebrovascular Permeability to Methotrexate . . . ", CA108(3):15739v, 1982.
Neuwelt, E. A. et al., "Characterization of a New Model of $G_{M2}$-Gangliosidosis (Sandhoff's Disease) in Korat Cats", *J. Clin. Invest.* 76:482–490 (1985).
Neuwelt, E. A., et al. "Osmotic Blood–Brain Barrier Opening to IgM Monoclonal Antibody in the Rat", *Am. J. Physiol.* 250:R875–883 (1986).
Neuwelt, E. A., et al., "Cerebrovascular Permeability and Delivery of Gentamicin to Normal Brain and Experimental Brain Abscess in Rats", *J. Neurosurg.* 61:430–439 (1984).
Neuwelt, E. A., et al., "Osmotic Blood–Brain Barrier Modification: Monoclonal Antibody, Albumin, and Methotrexate Delivery to Cerebrospinal Fluid and Brian", *Neurosurgery*, 17:419–423 (1985).
Williams, D. A. et al., "Introduction of New Genetic Material into Pluripotent Haematopoietic Stem Cells of the Mouse", *Nature*, 310:476–480 (1984).
Sorge, J. et al., "Amphotropic Retrovirus Vector System for Human Cell Gene Transfer", *Molecular and Cellular Biology*, vol. 4, No. 9, 1/30–1/37 (1984).
Miller, A. D., et al., "A Transmissible Retrovirus Expressing Human Hypoxanthine Phosphoribosyltransferase (HPRT): Gene Transfer into Cells Obtained From Humans Deficient in HPRT", *Proc. Natl. Acad. Sci.*, 80:4709 4713 (1983).
O'Dowd, B. F., et al. "Isolation of cDNA Clones Coding for the Beta Subunit of Human Beta Hexesaminidase", *Proc. Natl. Acad. Sci.* 82:1184–1188 (1985).
Sage, M. R., "Blood–Brain Barrier: Phenomenon of Increasing Importance to the Imaging Clinician"; *Am. J. of Roentgenology* 138:887–898 (1982).
Neuwelt, E. A., et al., "Growth of Human Lung Tumor in the Brain of the Nude Rat as a Model to Evaluate Antitumor Agent Delivery Across the Blood–Brian Barrier", *Cancer Research*, 45:2827–2833 (1985).
Mann, R., et al., "Construction of a Retrovirus Packaging Mutant and its Use to Produce Helper–Free Defective Retrovirus", *Cell* 33:153–159 (1983).
Greig, N., "Chemotherapy of Brain Metastases: Current Status", *Cancer Treatment Reviews*, 11, 157–186 (1984).
Sharkey, R. M., et al., "Factors Influencing Anti-Antibody Enhancement of Tumor Targeting with Antibodies in Hamsters with Human Colonic Tumor Xenografts", *Cancer Research*, 48:2005–2009 (1988).
Hiesiger, E. M., et al., "Opening the Blood–Brian and Blood–Tumor Barriers in Experimental Rat Brain Tumors: The Effect of Intracarotid Hyperosmolar Mannitol on Capillary Permeability and Blood Flow", *Ann. Neurol.*, 19:50 59 (1986).
Neuwelt, E. A., et al., "Permeability of Human Brain Tumor to $^{99m}$Tc-glucoheptonate and $^{99m}$Tc-albumin", *J. Neurosurg.*, 65:194–198 (1986).
Williams, D. A. et al., "Somatic Gene Therapy", *J. Clin. Invest.*, 77:1053–1056 (1986).

*Primary Examiner*—Mark L. Bell
*Assistant Examiner*—David M. Brunsman
*Attorney, Agent, or Firm*—Klarquist, Sparkman, Campbell, Leigh and Whinston

[57] ABSTRACT

A method for treating genetic and acquired brain disorders is disclosed in which genetic material is introduced into the blood stream for delivery to the brain. Prior to delivery, the interendothelial structure of the BBB is chemically altered to permit passage of the genetic material therethrough. This is accomplished through osmotic disruption of the BBB by administration of suitable chemical agents. Prior to administration, the genetic material can be inserted within the genome of a viral vector preferably incapable of replication in vivo. After crossing the blood brian barrier, the vector containing the genetic material enters the brain tissues where it delivers in a site-specific manner the genetic material in order to control adverse effects of the disease caused by defective genes. After delivery of the genetic material, the replication-defective character of the viral vector prevents its reproduction.

6 Claims, No Drawings

METHOD FOR THE DELIVERY OF GENETIC MATERIAL ACROSS THE BLOOD BRAIN BARRIER

This invention was made with Government support under a grant from the Veterans Administration. The Government has certain rights in this invention.

BACKGROUND OF THE INVENTION

The present invention generally relates to the treatment of genetic and metabolic brain disorders, and more particularly to a method for treating genetic and neurodegenerative diseases involving the delivery of corrective genetic materials into the brain.

A large variety of genetic brain disorders, such as Tay-Sach's disease, Alzheimer's disease and Parkinsonism, have been detected, researched and classified. As early as 1902, Sir Archibald Garrod first recognized genetic enzyme deficiency diseases and classified them as "inborn errors of metabolism." Since that time, extensive research has been conducted on the treatment of genetic brain disorders.

For example, in the last twenty-five years, over 360 specific catabolic enzyme deficiency diseases have been characterized. Recent biochemical and genetic research has identified the causes of more than 120 of these diseases, as discussed in McKusick, V. A., *Mendelian Inheritance in Man,* John Hopkins University Press, Baltimore, Maryland, 1978.

Most diseases involving genetic enzyme deficiencies are characterized by motor and mental deterioration leading to early death. A major group or neurodegenerative genetic enzyme disorders involves diseases classified as "lysosomal storage diseases". Lysosomes are the principal cite of intracellular digestion. They consist of membrane-encapsulated vesicles containing more than forty acid hydrolases capable of degrading most biologically important macromolecules, as discussed in Dan, R. T. et al., "Lysosomes", *Essays in Biochemistry* 12:1-40, 1976. Lysosomal storage diseases result from either the deficiency or nonfunctionality of one or more of the lysosomal hydrolases. These disorders are further characterized by the accumulation of the glycosphingolipid or glycosoaminoglycan substrate of the deficient enzyme in the lysosome.

A wide variety of neurodegenerative lysosomal storage diseases exist, some of which are listed below in Table I.

TABLE I

| Disease | Enzyme Deficiency |
|---|---|
| SPHINGOLIPIDOSES: | |
| GM$_1$ gangliosidosis | β-Galactosidase |
| GM$_2$ gangliosidosis: | |
| Classical Tay-Sachs | Hexosaminidase A |
| sandhoff's Variant | Hexosaminidase A & B |
| AB Variant | GM$_2$ activator |
| Metachromatic Leukodystrophy | Arylsulfatase A |
| Krabbe Disease | Galactocerebrosidase |
| Fabry Disease | α-galactosidase A |
| Gaucher Disease | β-glucosidase |
| Niemann-Pick | Sphingomyelinase |
| MUCOPOLYSACCHARISOSES: | |
| Hurler and/or Scheie | α- Iduronidase |
| Hunter Syndrome | Iduronate Sulfatase |
| Sanfilippo Disease: | |
| Type A | Heparin-N—sulfamidase |
| Type B | α-N—Acetylglucosaminidase |
| Type C | Heparin-N—Acetyl-transferase |
| Type D | α-N—glucosamine-6-sulfatase |
| Marguio Disease: | |
| Type A | Galactosamine-α-sulfate sulfatase |
| Type B | β-Galactosidase |
| Maroteaux-lamy | Arylsulfatase B |
| Sly Disease | β-Glucuronidase |
| DiFerrante | Glucosamine-6-sulfate sulfatase |

Most of the diseases listed in Table I actually involve several genotypic and phenotypic variations which have been grouped together on the basis of the defective enzyme.

Research involving genetic enzyme deficiencies has had a significant impact on reproductive counseling. It is now possible in many cases to reliably detect carrier heterozygotes as well as prenatally diagnose defective fetuses. Unfortunately, prenatal diagnosis is complicated by the fact that each disease is rare. Thus, at-risk carrier couples are often not identified until after an affected child is diagnosed.

In addition, some enzyme deficiency diseases may affect certain subpopulation groups more than others. For example, it is now possible to detect at an early stage the existence of Tay-Sachs disease in individuals of Ashkenazi Jewish ancestry However, even when effective screening programs for such diseases exist, they may not be used because of moral or religious convictions. Likewise, elective abortion is not always an acceptable consideration for similar reasons.

While carrier detection and prenatal diagnosis has had some impact in minimizing the number of individuals afflicted with genetic enzyme deficiency diseases, many problems still exist. A need therefore exists for an effective therapeutic program to control genetic enzyme deficiencies in patients having these diseases.

A variety of methods have been used to treat patients having genetic enzyme deficiencies, including lysosomal storage diseases. Current research indicates that the etiology of these U diseases at least partially results from a decreased concentration of the deficient enzyme product, as discussed in Barranger, J. A., "Feasibility of Enzyme Replacement in Brain: An Overview.", *Advances in the Treatment of Inborn Errors of Metabolism,* John Wiley, London, 1982. Therefore, a possible therapeutic strategy would be to provide enough of the deficient enzyme product to restore its concentration to normal levels Another possible theory explaining the pathogenesis of lysosomal storage diseases involves accumulation of the substrate of the affected enzyme Thus, alternative therapeutic strategies might include methods of reducing the concentration of excess enzyme substrate. Methods of accomplishing this involve dietary therapy and chelation of stored metabolites, as well as other methods which decrease the synthesis of the substrate by metabolic inhibition. While these methods have met with success in treating certain diseases (e.g., phenylketonuria), a large number of diseases remain which are not amenable to this type of treatment. In certain diseases, the excess substrate is an essential metabolite that is not readily regulated, and is synthesized throughout the body.

The treatment of genetic lysosomal storage diseases must therefore be approached from a dual standpoint: (1) the control of excess substrate accumulation: and (2) increasing the level of deficient enzymes. To accomplish these goals, a third category of therapeutic treatment may be possible which is called "enzyme replacement therapy." Using this method of treatment, properly administered exogenous enzymes gain access to substrate-engorged lysosomes via fusion with a primary lysosome. The administered enzyme can then restore the normal catabolic function of the affected lysosome. However, there are several problems associated with enzyme replacement therapy, described as follows:

1 *Enzyme Delivery Problems*

A major problem involving the delivery of exogenous enzymes is that of the blood brain barrier (BBB). The BBB is a capillary barrier comprising a continuous layer of endothelial cells which are tightly bound. The BBB excludes molecules in the blood from entering Z5 the brain on the basis of both molecular weight and lipid solubility, as described in Neuwelt, E. A. et al, "Is There A Therapeutic Role For Blood-Brain Barrier Disruption? ", *Ann. Int. Med.* 93:137-139, 1980: Rapoport, S. I., *Blood-Brain Barrier in Physiology and Medicine*, Raven Press, N.Y. 1976. For example, the BBB normally excludes molecules with a molecular weight greater than 180 daltons. Similar exclusion occurs on the basis of lipid solubility.

One method of passing agents through the BBB involves osmotic disruption of the barrier by the administration of hypertonic mannitol or other agents, as described in Neuwelt, E. A., "Osmotic Blood-Brain Barrier Modification: Monoclonal Antibody, Albumin, and Methotrexate Delivery to Cerebrospinal Fluid and Brain", *Neurosurgery*, 17:419-423, 1985: Rapoport, supra. Disruption of the BBB using this method is caused by a shrinkage of the cerebrovascular endothelial cells, which increases the permeability of the interendothelial junctions.

However, numerous problems exist when exogenous enzymes are administered. Tests indicate that low amounts of enzymes are actually delivered, since organ-derived, purified lysosomal enzymes injected into a patient's blood stream are rapidly cleared, with a half life in the range of several minutes as described in Ratazzi, N., "Enzyme Therapy in Lysosomal Storage Diseases: Current Approaches.", *Human Genetics - Part B: Medical Aspects* 573-587, 1982. Organ biopsies and radioimmunodiffusion assays demonstrate that the exogenous enzyme is found mainly in the liver, with only minimal activity detectable in extrahepatic tissues. This rapid clearance is most likely caused by hepatic receptors which recognize terminal mannosyl and N-acetyl-glucosaminyl residues on the lysosomal enzymes.

Another problem involving the direct delivery of Z5 exogenous enzymes is the likelihood that a recognition marker will be required for proper enzyme uptake, as indicated in Hickman, S. et al, "A Recognition Marker Required For Uptake of Lysosomal Enzyme By Cultured Fibroblasts.", *Biochem.Byophys. Res.Comm.* 57:55-61, 1974. Accordingly, effective enzyme replacement therapies will not only require administration of a highly stable, very specific enzyme which is protected from hepatic clearance, but the enzyme must also bind to a receptor with a high affinity that will deliver the enzyme to the proper intracellular compartment.

2.*Problems Involving the Availability of Enzyme Supplies*

Many of the needed enzymes required for effective enzymatic therapy are difficult and costly to obtain. Likewise, such enzymes frequently must be administered at numerous intervals, requiring substantial amounts of materials to be obtained. It may also take months or even years of enzyme administration for the treatment to be effective.

3. *Problems Involving Protection of the Enzyme*

In addition to protecting the administered enzymes from rapid renal clearance, the enzymes must also be protected from the patient's immune system, as described in Poznanski, M. J., "Enzyme-Protein Conjugates: New Possibilities For Enzyme Therapy", *Pharmac. Ther.* 21:5-76, 1983. Adverse immunological responses are particularly evident when the administered enzymes are derived from fungal or bacterial sources. Also, there is the possibility of acute enzyme toxicity caused by the administration of large doses of enzymes. This toxicity may be manifested in acute hyperproteinemia.

Thus, there are numerous problems associated with the direct administration of purified exogenous enzymes in the treatment of lysosomal storage diseases. There have been human Z5 trials involving this method, all of which have met with minimal success. A key problem remaining in exogenous enzyme replacement therapy is the delivery of enzymes across the blood brain barrier, as described above. In order to overcome this problem, another treatment method has been tested which involves direct tissue transplantation.

The first use of organ replacement therapy in a genetic storage disease involved a spleen allograft in a patient having Gaucher's disease, as described in Groth, C. G. et al "Splenic Transplantation In a Case of Gaucher's Disease", *Lancet* 1260-1264, 1971. However, no clinical improvement in the patient was noted, and death occurred several months following a severe tissue incompatibility response Other tests were conducted involving kidney grafts and liver transplantations, all of which were minimally successful.

Thus, organ and tissue transplantation has not been effective in treating lysosomal storage diseases that affect the CNS. Transplanted organs do not appear to synthesize and/or release sufficient quantities of enzymes in order to control the disease. Even if the transplantation did result in circulation of sufficient amounts of enzymes as has been the case with bone marrow transplants in some of the mucopolysaccharidoses, there is still the problem of delivery across the BBB.

A need therefore exists for a treatment therapy effective in controlling the effects of genetic enzyme deficiency diseases and other genetic and metabolic brain disorders, including Parkinsonism and Alzheime's disease. For example, in Parkinsonism, there is a deficiency of dopamine which may benefit from increased levels of the enzyme tyrosine hydroxylase. There is also some evidence that in Alzheimers's disease there is a deficiency of choline acetyl transferase (CAT). Finally, there is a need for a treatment therapy which Z5 minimizes the problems associated with traditional treatment methods. These problems include transport across the BBB, adverse immunological responses, rapid renal clearance and other physiological difficulties.

SUMMARY OF THE INVENTION

It is an object of the present invention to provide an effective method for treating genetic and acquired metabolic brain disorders. disorders which avoids adverse immunological side effects.

It is a further object of the invention to provide a method for treating genetic and acquired metabolic brain disorders which avoids renal clearance problems associated with the direct infusion of purified exogenous enzymes.

It is a further object of the invention to provide a method for treating genetic and acquired metabolic brain disorders which avoids problems inherent in methods involving tissue transplantation.

It is a further object of the invention to provide a method for treating genetic and acquired metabolic brain disorders which uses readily available, relatively inexpensive materials.

It is a still further object of the invention to provide a method for treating genetic and acquired metabolic brain disorders which involves providing corrective genetic material to the brain in order to effectively treat the disorder on a molecular level.

To accomplish these objectives, a method for treating genetic and acquired metabolic brain disorders (e.g. neurodegenerative lysosomal storage diseases) is disclosed in which corrective genetic material is inserted directly into the Z5 brain. This is preferably accomplished using a specially prepared viral vector containing corrective genetic material. It is desirable that the virus be incapable of replication so that delivery of the virus can occur without the formation of viral progeny. Prior to delivery of the viral vector into the brain, the interendothelial structure of the BBB is chemically altered to increase its permeability. This is preferably chemical agents. The viral vector is then permitted to enter the brain tissues where it delivers in a site-specific manner the corrective genetic material in order to control adverse effects of the disease caused by defective genes.

Using this procedure, the pathogenesis of neurodegenerative enzyme deficiency diseases and other brain disorders would be eliminated. Likewise, excessive renal clearance, adverse immunological responses, and other problems associated with tissue transplantation or direct introduction of exogenous enzymes are avoided.

These and other objects, features, and advantages of the invention will be described hereinafter in the following detailed description of a preferred embodiment.

DETAILED DESCRIPTION

The present invention involves a treatment method in which the blood brain barrier is chemically altered to allow the passage of corrective genetic material. Preferably, the corrective genetic material will be carried by a vector such as a virus. This strategy completely bypasses many of the problems inherent in transplantation and enzyme replacement techniques. It instead focuses on the cause of the problem, namely, a mutant gene.

A particularly useful method involves the packaging of corrective genetic material in a viral vector as illustrated by the following discussion.

Preparation of a Retrovirus Vector

In gene replacement therapy, the replaced gene must not only be delivered to the proper tissue, but must achieve access to the proper intracellular regions. This can be accomplished by using a virus or retrovirus (hereinafter referred to as a "viral vector").

The genome of a retrovirus includes the gag, pol and env genes. Gag codes for viral capsid proteins, env for proteins that will be incorporated into the outer membrane, and pol for the reverse transcriptase and integrase enzymes.

Infection of a host cell by a retrovirus results in the release of two copies of the single stranded retroviral RNA genome, and the enzymes reverse transcriptase and intergrase contained within the virion core. Reverse transcriptase transcribes the RNA genome into an RNA-DNA heteroduplex and then into a DNA duplex forming two complete long-terminal repeats (LTR's) in the process. A covalently closed circle is then formed by non-homologous recombination between the distal regions of the two LTRs. A site is recognized by the retroviral enzyme integrase which catalyzes insertion of the viral genome into the host cell genome. This insertion is site specific with respect to the retrovirus, but random with respect to the host.

Once the viral genome is integrated into the host cell genome, transcription is initiated and viral genes are under the Z5 influence of a retroviral promoter. The retroviral genome contains two sites which are referred to as the splice donor (S.D.) and splice acceptor (S.A.) sites. During transcription, the S.D. site is capable of directing the gag, pol genetic regions to be spliced out. This results in transcription of the is only about 50% effective. As a result, RNA polymerase reads through the S.D. site and the full length genomic RNA containing the gag and pol gene region is transcribed. Translation of these transcripts forms the essential retroviral proteins which enable formation of the viral particle. It is important to note that only the genomic RNA containing the encapsidation site is incorporated into the virion.

When using a retroviral vector for the transfer of genes into cells, one of the concerns that must be dealt with is the undesirable effect of replicating viruses. One means of eliminating this problem has been the construction of trans-defective, cis-active retroviral vectors. The cis portion of the retroviral genome includes the long terminal repeat (LTR) sequences, the primer binding site, the polypurine tract, and the $\Omega$ sequences necessary for viral RNA packaging (encapsidation). The other regions of the retroviral genome necessary for replication are referred to as trans portions. These regions encode the viral proteins gag, pol and env, along with the control elements and splice donator/acceptor sites necessary to express them. Thus, a cis-active, trans-defective retrovirus is one in which a trans region gene such as gag, pol or env has been partially or completely deleted or replaced with another gene. Such a retrovirus is able to undergo reverse transcription and integration as a DNA provirus. The integrated provirus can be transcribed by the RNA polymerase of the host cell to yield full length (and subgenomic) polyadenylated viral RNAs capable of being incorporated into virions that bud from the cell. This trans-defective retrovirus, however, does not its own propagation and is therefore replication defective.

As described in Wigler, M., et al, "Transformation Of Mammalian Cells With an Amplifiable Dominant Acting Gene", *Proc. Natl. Acad. Sci.* 77:3567-3571, 1980, trans-defective retroviruses have been utilized as vectors for the transfer of cloned selectable and non-selectable genes. In general, the gene of interest is inserted into the retroviral sequence coding for the genomic RNA in the place of the gag-pol trans gene, and a selectable marker gene is inserted into the sequence encoding the subgenomic mRNA in place of the env trans gene. A commonly used marker is the neo gene, which confers G418 resistance in eukaryotes and kanamycin resistance in bacteria.

Transfection of an appropriate cell with a vector retrovirus will result in expression of the gene and selectable marker genes under the control of the retroviral transcriptional regulators, but will not result in the release of retroviral progeny because of the lack of essential gene products.

One consequence of the inability of the vector retrovirus to propagate itself is that a helper virus is required to generate the vector retrovirus. When an appropriate cell is infected with the trans-defective vector retrovirus, it is superinfected with a trans-active helper virus which provides deficient viral products and allows packaging of the vector RNA. The need for a helper virus has been overcome by the construction of cis-defective retroviruses which are packaging mutants. The region of this mutation is distal of the splice donator site and upstream of the transcriptional start of the gag, pol regions. The mutation region contains the site which is essential for the encapsidation of the viral genome. Thus, a packaging cell line contains a deficient retrovirus genome but does contain the helper virus gag, pol and env gene products which can be used to package retroviral RNAs into virions.

Retroviral vectors are only suitable for the delivery of cDNA clones. Such clones are mRNA complements which do not contain the introns of the full-length genomic genes. This limitation is a result of size constraints (approximately 8 kilobase pairs) and the fact that genomic clones inserted into retroviral vectors will be spliced down to the mRNA complement during the first retroviral generation.

cDNA clones can be created from purified mRNA in a variety of ways such as by the addition of a polythymidine primer to the purified mRNA template, as outlined in Horwich, A. L. et al, "Strategies For the Molecular Cloning Of Low Abundance Messenger RNA's", *Molecular Basis Of Lysosomal Storage Disorder*, Academic Press, 1984. DNA polymerase I is then used to synthesize the negative strand of DNA. Following completion of this reaction, the original RNA component of the previously formed heteroduplex can be preferentially degraded by the addition of alkali. A second primer is not required to continue the reaction because the 3' end of the newly synthesized DNA strand is able to bend back on itself to form a "hairpin loop" primer. Reverse transcriptase also has a DNA polymerase function and is able to synthesize the second DNA strand using Z5 the first strand as a template. The reaction is completed by removing the hairpin loop through the addition of S1 nuclease which specifically cleaves single stranded nucleic acids. It should be noted that cDNA clones formed in this manner are always deficient of a short stretch complementary to the 5' region of the mRNA because of the removal of the hairpin loop region. Another method for generating full length duplex cDNA involves the enzyme RNAse H. This enzyme nicks the RNA strand of an RNA-DNA heteroduplex. In this procedure the first strand cDNA synthesis is carried out as previously described, then the RNA is removed by treating the heteroduplex with RNAse H and subsequently using DNA polymerase I for second strand synthesis.

Once a duplex cDNA of interest has been obtained, the next step is to generate a large number of copies. This is accomplished by inserting the clone either into a plasmid vector containing a selectable marker and transforming a bacterial cell line or by inserting the clone into a bacteriophage and transfecting the cell line. The most commonly used bacteriophages are the λgt10 and λgt11 vectors. Libraries constructed with these vectors have the advantages of being more easily screened as well as the fact that transfections are accomplished at a higher rate of efficiency than transformations.

The first step in the plasmid procedure involves cleavage of the vector with a Type II restriction endonuclease. EcoRI is one example of this type of restriction endonuclease. EcoRI recognizes a specific six base pair sequence of DNA and catalyzes a specific cleavage of the DNA within the recognition sequence. This procedure creates four long base "sticky ends". Because EcoRI always creates the same ends and complementary DNA is capable of annealing, one method of inserting a clone into vector DNA is simply to cleave both the vector and the clone with the same restriction endonuclease and then allow the clone and vector to anneal on the basis of the complementary nature of the "sticky ends".

An alternative procedure to construct a plasmid vector is entitled the "complementary tailing" method. In this method, the vector is opened with a restriction endonuclease and complementary nucleotide tails are added to the vector and insert DNA in separate reaction mixtures with dioxynucleotidyl transferase. Finally, the insert is annealed to the vector on the basis of the complementary tails, and the gaps are covalently closed with ligase. It should be noted that both of these methods rely on selectable markers in the vector plasmid to isolate the vectors into which the clone has been properly inserted as opposed to the vector simply recombining with itself or other plasmids.

A popular method of cDNA cloning is described in Okayama, H., et al, "High-Efficiency Cloning of Full-Length cDNA", *Molecular and Cellular Biol.* 2:161-170, 1982. This method combines the synthesis of duplex cDNA using the above complementary tailing method with the actual cloning into a plasmid vector for amplification. It involves annealing mRNA to an oligo dT tail already contained in a plasmid and then reverse transcribing the cDNA directly into the vector. After closure of the plasmid with a linker that is complementary to both the vector and to a synthetic tail on the cDNA, the original mRNA can be removed with E. coli RNAse A, subsequently the second strand synthesis is carried out by DNA polymerase I. Z5 The advantage of this method is that there is no loss of the insert due to removal of the hairpin loop because none is required.

Using the aforementioned techniques, a retrovirus can be prepared which includes a suitable cDNA clone for use in the treatment of genetic brain disorders or other metabolic diseases.

Once the viral vector is prepared, it must be able to pass through the BBB. To accomplish this, the vector is directly administered to the patient in conjunction with osmotic disruption of the BBB. Administration of the vector should be completed within 1-2 minutes after BBB disruption since disruption occurs for only a short period of time. Osmotic disruption of the BBB may be accomplished using hypertonic mannitol or other hypertonic solutions. Specific methods of BBB modification are discussed in Neuwelt, E. A., "Osmotic Blood-Brain Barrier Modification: Monoclonal Antibody, Albumin, and Methotrexate Delivery to Cerebrospinal Fluid and Brain", supra. Once entry of the vector is accomplished, its corrective genetic material is incorporated in affected tissues. The genetic material is typically only incorporated in replicating cells. Replication occurs slowly in glia and little- if at all in neurons. Thus, growth or maturation factors (i.e. glial maturation factor, or nerve growth factor) may also be needed for the corrective gene material to be integrated. It is likely that only glia will be infected since mature neurons do not replicate. However, lysosomal enzymes are partially released into the extra-cellular space and then taken up by other cells via the mannose 6 phosphate receptor which is present on neurons. Therefore, infected glia may supply enzyme to neurons.

Delivery Across the Blood Brain Barrier

The successful delivery of a virus across the blood brain barrier of a subject organism according to the present invention is illustrated by the following procedure for the intracarotid delivery of S Herpes virus into the brain tissues of laboratory rats.

A. Methods and Materials

Adult female, Sprague-Dawley rats were anesthetized with sodium pentobarbital (50mg/kg, intraperitoneal). A catheter filled with sodium heparin in isotonic 0.9% NaCl was tied into the right external carotid artery for retrograde infusion. Five minutes prior to BBB modification, Evans blue was administered intravenously (2%: 2ml/kg). Mannitol (25%) warmed to 37° C. was then infused for 30 seconds cephalad into the right internal carotid artery through the right external carotid artery catheter at a rate of 0.12ml/sec. As described herein, mannitol will increase the permeability of the BBB. In control animals, 0.9% NaCl solution instead of mannitol was used at an identical rate and volume.

Next, U.V. inactivated „S-Herpes virus was administered at three different dosage levels as an intracarotid bolus, over a 30 second time period one minute after mannitol/saline infusion One hour later, a serum sample was collected and the rat perfused with 0.9% sodium chloride to clear the vascular system of radioactivity. Samples were then collected from the rat brain including the contralateral hemisphere (LH), disrupted or right hemisphere (RH), and liver Z5 (L) The samples were then weighed, solubilized, and counted in a liquid scintillation cocktail for activity. To determine the amount of activity associated with protein (virus), samples were weighed and homogenized in 0.5ml saline and an aliquot or homogenate was then added to an equal volume of 20% trichloroacetic acid. The samples were centrifuged at 1200 x g for 30 minutes and the resultant fractions counted in the cocktail for activity.

B. Results and Conclusions

The experimental results for three different dosages of 3 5S-Herpes virus are described below in Tables II, III and IV.

TABLE II

DOSE: $1.0 \times 10^6$ cpm or $4.3 \times 10^7$ pfu

| MANNITOL | | | | | | | |
|---|---|---|---|---|---|---|---|
| LH | RH | LIVER | SERUM | % DEL | TCA-RH | TCA-Liver | CLEAR |
| 2,253 | 10,093 | 21,815 | 4,125 | 1.0 | — | — | 81 |
| 1,514 | 7,803 | 29,370 | 5,745 | 0.8 | — | — | 88 |
| 804 | 6,730 | 25,692 | 5,745 | 0.7 | 84 | 82 | 89 |
| 915 | 8,855 | 26,623 | 5,775 | 0.9 | 92 | 86 | 87 |
| 1,589 | 12,627 | 30,749 | 4,890 | 1.3 | 88 | 83 | 87 |
| 1,317 | 10,199 | 35,960 | 5,170 | 1.0 | 91 | 81 | 90 |
| 1,399 | 9,243 | 28,368 | 5,238 | 0.95 | 89 | 83 | 87 |

| NORMAL SALINE | | | | | | | |
|---|---|---|---|---|---|---|---|
| LH | RH | LIVER | SERUM | % DEL | TCA-RH | TCA-Liver | CLEAR |
| 1,301 | 4,110 | 36,544 | 6,160 | 0.40 | 63 | 78 | 56 |
| 1,711 | 3,980 | 56,984 | 3,445 | 0.38 | 85 | 80 | 70 |
| 1,506 | 3,980 | 46,764 | 4,803 | 0.39 | 74 | 79 | 63 |

LEGEND:
LH: Nondisrupted or left hemisphere (cpm/gm)
RH: Disrupted or right hemisphere (cpm/gm)
Liver: Expressed in cpm/gm
Serum: Expressed in cpm/ml serum
% DEL: Per cent delivered dose per gram of brain in disrupted hemisphere
TCA-RH: Per cent precipitable counts using trichloroacetic acid in disrupted brain
TCA-LIVER: Per cent precipitable counts using trichloroacetic acid in liver
CLEAR: Per cent clearance of activity from serum
$\frac{\text{Post-perfusion}}{\text{Pre-perfusion}} \times 100$
Mean value of columns are underlined

TABLE III

DOSE: $2.0 \times 10^6$ cpm or $1.09 \times 10^8$ pfu

| LH | RH | LIVER | SERUM | % DEL | TCA-RH | TCA-Liver | CLEAR |
|---|---|---|---|---|---|---|---|
| | | | MANNITOL | | | | |
| 2,297 | 31,534 | 71,331 | 10,590 | 1.6 | 91 | 81 | 93 |
| 2,406 | 26,838 | 77,880 | 11,410 | 1.3 | 91 | 80 | 94 |
| 2,352 | 29,186 | 74,606 | 11,000 | 1.45 | 91 | 81 | 94 |

TABLE III-continued

| DOSE: 2.0 × 10⁶ cpm or 1.09 × 10⁸ pfu | | | | | | | |
|---|---|---|---|---|---|---|---|
| LH | RH | LIVER | SERUM | % DEL | TCA-RH | TCA-Liver | CLEAR |
| NORMAL SALINE | | | | | | | |
| 2,555 | 7,567 | 54,043 | 8,365 | 0.38 | 78 | 77 | 81 |
| 525 | 5,126 | 62,801 | 11,350 | 0.26 | 83 | 80 | 90 |
| 1,540 | 6,347 | 58,422 | 9,858 | 0.32 | 81 | 79 | 86 |

(Legend same as Table II)

TABLE IV

| DOSE: 3.0 × 10⁶ cpm or 1.68 × 10⁸ pfu MANNITOL | | | | | | | |
|---|---|---|---|---|---|---|---|
| LH | RH | LIVER | SERUM | % DEL | TCA-RH | TCA-Liver | CLEAR |
| 0 | 44,490 | 101,174 | 15,335 | 1.5 | 87 | 81 | 86 |
| 3,626 | 53,694 | 102,269 | 19,260 | 1.8 | 92 | 77 | 92 |
| 1,836 | 49,092 | 101,722 | 17,298 | 1.65 | 90 | 79 | 89 |

(Legend same as Table II)

The animals undergoing intracarotid (IC) saline and subsequent IC virus at dosages of 1.0 and 2.0 x 10° cpm had ipsilateral hemisphere concentrations which corresponded to 0.39% and 0.32% of the delivered dose. Contralateral hemisphere values were 0.15% and 0.08% of the delivered doses respectively. This suggests about a three-fold increase in non-specific adherence of virus to brain vasculature due to intracarotid administration. Clearance of radioactivity from serum averaged approximately 85% in all groups suggesting modest contamination in samples due to blood. Samples were not corrected for residual activity as determined by clearance values.

In barrier modified animals, a definite increase in viral concentration was evident in the ipsilateral hemisphere. At a dosage of $1.0 \times 10^6$ cpm there was a 2.32 fold increase in disrupted brain when comparing mannitol with normal saline concentrations. In animals given $2.0 \times 10^6$ cpm, the corresponding increase was 4.6 fold. In addition, the per cent delivered dose per gram of tissue in disrupted brain was 0.95%, 1.45%, and 1.65% for 1, 2, and $3 \times 10^6$ cpm of virus. When the values were corrected for non-specific binding as determined from the normal saline values, the delivered doses were 0.56%, and 1.13% for 1 and $2 \times 10^6$ cpm dosages (saline values for 3 x 10° cpm were not available). This again reflects an increase in viral delivery to the brain after barrier modification. Precipitation of radioactivity from disrupted brain averaged 90% in the three dosage groups, suggesting that the radioactivity remains associated with the protein (virus).

The above experiments show that the protein components of herpes virus are delivered across the BBB but do not prove delivery of assembled virus. To show the penetration of assembled virus through the BBB, the following electron microscopy (EM) studies were done.

In Vitro Extraction of $^{35}$ S-labeled Herpes Virus From Brain In Preparation for Electron Microscopy Studies Normal rat brain was homogenized in saline at a w:v ratio of 1:5 and the homogenate was spiked with $1.0 \times 10^5$ cpm of „S herpes virus (UV inactivated). The sample was incubated at 37° C. for 20 minutes to allow for any nonspecific binding of virus to brain protein. The sample was centrifuged for 20 minutes at 600 x g to pellet out large insoluble particulate matter and this fraction was counted for activity. It contained 60% of administered dose. The supernatant was divided into three fractions (400, 400, and 600 μl) to which 100pl of antiherpes virus antibody was added. The mixtures were allowed to incubate for 20 minutes at 37° C. to allow for antibody binding. Then 100 μl of protein A sepharose (specific for IgG complex added to each sample and incubated for 18 hours at 4° C. The samples were centrifuged at 1200 x g for 20 minutes to pellet out protein A sepharose and the resultant fractions counted.

Result: The supernatants contained 61%, 63%, and 65% Z5 (mean 63%) and the pellets 39%, 37%, and 35% (mean 37%). This suggests that under these experimental conditions it is possible to extract herpes virus from a spiked brain homogenate using protein A bound to sepharose beads.

In vivo Extraction of Herpes Virus from Brain for Electron Microscopy

The rat blood brain barrier was modified and the animal given intracarotid non-radioactive herpes virus ($5 \times 10°$ pfu) using the identical conditions as described in the S delivery study protocol. The virus was UV inactivated. At sacrifice, the brain was removed and the disrupted and nondisrupted hemispheres collected.

The in vitro test conditions as described above were carried out on a contol homogenate spiked with $1 \times 10^9$ pfu, disrupted hemisphere and non-disrupted hemisphere from the experimental animal. As an additional control, aliquots of virus spiked brain and disrupted brain were incubated with sepharose not bound to protein-A at the appropriate time point.

Results: There was no binding of virus to plain sepharose beads as shown by electron microscopy. Electron micrographs showing viral particles were only seen in disrupted brain using protein-A sepharose and in virus spiked brain using protein-A sepharose.

The foregoing studies therefore strongly suggest delivery of intact virus across the BBB.

Having accomplished BBB transport of an intact virus as described above, the foregoing procedure may be used to transport any suitably prepared virus, retrovirus or similarly sized particle across the BBB. Retrovirus preparation may be "Construction of a Retrovirus Packaging Mutant and Its Use to Produce Helper-Free Defective Retrovirus", Cell, 33: 153–159, 1983; and Sorge, J. et al., "Amphotropic Retrovirus Vector System For Human Cell Gene Transfer", Molecular and Cellular Biology, 4:1730–1737, 1984. Furthermore, it has been proven that retroviruses carrying selected genetic material will transfect living tissues in vitro. Williams, D. A., et al, "Introduction of new genetic material into pluripotent haematopoietic stem cells of the mouse", *Nature,* 310:476–480, 1984.

Thus, the present invention represents an important advance in the treatment of genetic and/or acquired metabolic brain disorders including, but not limited to, Tay-Sach's problems associated with prior treatment methods, including the direct infusion of exogenous enzymes and direct tissue transplantation.

Having herein described a preferred embodiment of the present invention, it is anticipated that suitable modifications may be made by those skilled in the art within the scope of the invention. For example, genetic material could be transported across the BBB apart from a vector or as a part of an assembled group of molecules that contains the genetic material. The foregoing examples indicate that such groups of molecules, if viral sized (30–300nm), should be transportable across the BBB by the same mechanism as viruses. Thus, the invention shall only be construed in accordance with the following claims.

What is claimed is:

1. A method for the delivery and 2 incorporation of corrective genetic material into the cellular tissues of the brain of a human subject or other warm blooded animal subject for the treatment of genetic and acquired metabolic brain disorders, the method comprising the steps of:

inserting genetic material designed to correct disorders of the brain into a virus;

chemically disrupting the blood brain barrier of the subject so as to increase the permeability thereof;

administering said virus containing said genetic material into the bloodstream of said subject for incorporation into the cellular tissues of said brain, said virus crossing the blood brain barrier of its increased permeability; and allowing said virus to deliver said genetic material into said cellular tissues of said brain, said genetic material being incorporated into said cellular tissues in order to treat said disorders of said brain.

2. The method of claim 1 wherein said virus is administered to said subject intravenously.

3. The method of claim 1 wherein said virus is administered to said subject intra-arterially.

4. The method of claim 1 wherein said chemical disruption of said blood brain barrier involves osmotic blood brain barrier modification through the administration of a pharmaceutically effective, non-toxic hypertonic solution.

5. The method of claim 4 wherein said hypertonic solution comprises a material selected from the group consisting of mannitol, arabinose, and glycerol.

6. The method of claim 1 wherein said administering of said virus is accomplished within about 1–2 minutes after said chemical disruption of said blood brain barrier.

* * * * *

UNITED STATES PATENT AND TRADEMARK OFFICE
CERTIFICATE OF CORRECTION

PATENT NO. : 4,866,042

DATED : September 12, 1989

INVENTOR(S) : Edward A. Neuwelt

It is certified that error appears in the above-identified patent and that said Letters Patent is hereby corrected as shown below:

Column 1, line 33, "group or" should be --group of--;

Column 1, line 39, "Dan" should be --Dean--;

Column 2, lines 46-47, "these (paragraph) U diseases" should be --these diseases--;

Column 3, lines 21-22, "entering Z5 the" should be --entering the--;

Column 3, lines 57-58, "of Z5 exogenous" should be --of exogenous--;

Column 4, line 27, "human Z5 trials" should be --human trials--;

Column 4, line 64, "Z5" should be omitted;

Column 5, lines 5-6, "brain disorders, disorders which avoids adverse immunological side effects." should be --brain disorders. It is another object of the invention to provide a method for treating genetic and acquired metabolic brain disorders which avoids adverse immunological side effects.--;

Column 5, line 29, "Z5" should be omitted;

UNITED STATES PATENT AND TRADEMARK OFFICE
CERTIFICATE OF CORRECTION

PATENT NO. : 4,866,042

DATED : September 12, 1989

INVENTOR(S) : Edward A. Neuwelt

It is certified that error appears in the above-identified patent and that said Letters Patent is hereby corrected as shown below:

Column 5, lines 36-37, "preferably chemical agents." should be --preferably accomplished through osmotic disruption of the BBB by the administration of suitable chemical agents.--

Column 6, line 24, "Z5" should be omitted;

Column 6, line 29, between words "the" and "is", insert --subgenomic RNA containing the env gene. However the S.D. site--;

Column 13, claim 1, line 25, "and 2 incorporation" should be --and incorporation--; and Column 14, claim 1, line 8, "barrier of" should be --barrier because of--.

Signed and Sealed this

Seventh Day of September, 1993

Attest:

BRUCE LEHMAN

Attesting Officer

Commissioner of Patents and Trademarks